United States Patent [19]

Lavanish

[11] 4,302,239
[45] Nov. 24, 1981

[54] 3-(5- OR 3-SUBSTITUTED-5- OR 3-ISOXAZOLYL)-1-ALLYL OR ALKYL-4-SUBSTITUTED-5-SUBSTITUTED OR UNSUBSTITUTED-2-IMIDAZOLIDINONES FOR CONTROLLING WEEDS

[75] Inventor: Jerome M. Lavanish, Akron, Ohio

[73] Assignee: PPG Industries, Inc., Pittsburgh, Pa.

[21] Appl. No.: 225,230

[22] Filed: Jan. 15, 1981

Related U.S. Application Data

[62] Division of Ser. No. 122,633, Feb. 19, 1980.

[51] Int. Cl.³ .................................... A01N 43/62
[52] U.S. Cl. .................................................. 71/88
[58] Field of Search ...................................... 71/88

[56] References Cited

U.S. PATENT DOCUMENTS 3,544,582  12/1970  Albrecht et al. .................. 260/307
3,773,780  11/1973  Metzger et al. ................. 260/306.8
3,847,935  11/1974  Moffett ............................ 260/309.7

FOREIGN PATENT DOCUMENTS 2727586  1/1979  Fed. Rep. of Germany .
5163170  6/1976  Japan .

Primary Examiner—Anton H. Sutto
Attorney, Agent, or Firm—Edward J. Whitfield

[57] ABSTRACT

Disclosed are compounds such as 3-[5-(1,1-dimethylethyl)-3-isoxazolyl]-1-methyl-4-hydroxy-2-imidazolidinone; their control of weeds such as johnsongrass; the process of making them; and intermediates for making them, the compounds being represented by a Formula I:

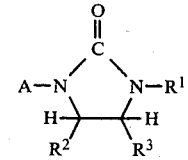

(I)

wherein A is

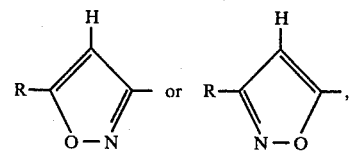

where R is an alkyl of up to six carbon atoms; an alkenyl of up to five carbon atoms; an alkynyl of up to five carbon atoms; a cycloalkyl selected from the group consisting of cyclopropyl, cyclobutyl, cyclopentyl, and cyclohexyl; a haloalkyl of up to six carbon atoms; $-R^4-O-R^5$, or $-R^4-S-R^5$, where $R^4$ is an alkylene of up to six carbon atoms and $R^5$ is an alkyl of up to six carbon atoms;

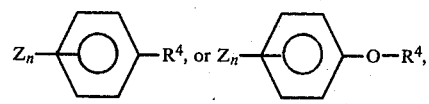

where Z is nitro ($NO_2$), chloro (Cl), bromo (Br), fluoro (F), or $R^5$, and n is 0, 1, 2, or 3; $R^1$ is an alkyl of up to three carbon atoms, or allyl; $R^2$ is hydroxy (OH), chloro (Cl) or bromo (Br); and $R^3$ is hydrogen (H), an alkyl of up to four carbon atoms, allyl, or hydroxy (OH).

4 Claims, No Drawings

3-(5- OR 3-SUBSTITUTED-5- OR 3-ISOXAZOLYL)-1-ALLYL OR ALKYL-4-SUBSTITUTED-5-SUBSTITUTED OR UNSUBSTITUTED-2-IMIDAZOLIDINONES FOR CONTROLLING WEEDS

This is a division of application Ser. No. 122,633, filed Feb. 19, 1980.

BACKGROUND OF THE INVENTION

1. Field of the Invention

The invention pertains to 3-[5- or 3-(alkyl, alkenyl, alkynyl, cycloalkyl, haloalkyl, alkoxyalkyl, alkylthioalkyl, optionally substituted phenylalkyl, optionally substituted phenoxyalkyl)-3- or 5-isoxazolyl]-1-alkyl or allyl, -4-hydroxy or halo, -5-alkyl, allyl, hydroxy, or unsubstituted 2-imidazolidinones, such as 3-[5-(1,1-dimethylethyl)-3-isoxazolyl]-1-methyl-4-hydroxy-2-imidazolidinone or 3-[3-(1,1-dimethylethyl)-5-isoxazolyl]-1-methyl-4-hydroxy-2-imidazolidinone; the intermediates for forming the compounds; the process for forming the compounds; and the control of the weeds with the compounds.

SUMMARY OF THE INVENTION

Compounds graphically represented by Formula I:

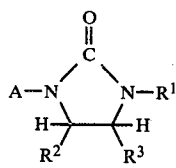
(I)

wherein A is

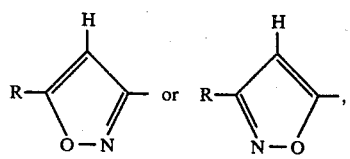

where R is an alkyl of up to six carbon atoms; an alkenyl of up to five carbon atoms; an alkynyl of up to five carbon atoms; a cycloalkyl selected from the group consisting of cyclopropyl, cyclobutyl, cyclopentyl, and cyclohexyl; a haloalkyl of up to six carbon atoms; $-R^4-O-R^5$ or $-R^4-S-R^5$, where $R^4$ is an alkylene of up to six carbon atoms and $R^5$ is an alkyl of up to six carbon atoms;

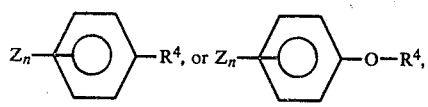

where Z is nitro ($NO_2$), chloro (Cl), bromo (Br), fluoro (F), or $R^5$, and n is 0, 1, 2, or 3; $R^1$ is an alkyl of up to three carbon atoms, or allyl; $R^2$ is hydroxy (OH), chloro (Cl) or bromo (Br); and $R^3$ is hydrogen (H), an alkyl of up to four carbon atoms, allyl, or hydroxy (OH) are useful herbicides. In particular, the compounds 3-[5-(1,1-dimethylethyl)-3-isoxazolyl]-1-methyl-4-hydroxy-2-imidazolidinone and 3-[5-(1,1-dimethylethyl)-3-isoxazolyl]-1-methyl-4,5-dihydroxy-2-imidazolidinone are particularly effective herbicides against weeds, particularly at very low rates of applications. The invention also concerns intermediates of Formula II described herein which are useful for forming the compounds, the processes for forming the compounds, and the method of controlling the weeds with the compounds.

DETAILED DESCRIPTION OF THE INVENTION

The novel agriculturally useful compounds are graphically represented by Formula I:

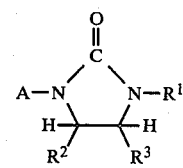
(I)

wherein A is

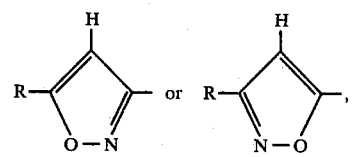

where R is an alkyl of up to six carbon atoms; an alkenyl of up to five carbon atoms; an alkynyl of up to five carbon atoms; a cycloalkyl selected from the group consisting of cyclopropyl, cyclobutyl, cyclopentyl, and cyclohexyl; a haloalkyl of up to six carbon atoms; $-R^4-O-R^5$ or $-R^4-S-R^5$, where $R^4$ is an alkylene of up to six carbon atoms and $R^5$ is an alkyl of up to six carbon atoms;

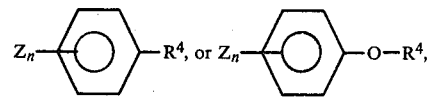

where Z is nitro ($NO_2$), chloro (Cl), bromo (Br), fluoro (F), or $R^5$, and n is 0, 1, 2, or 3; $R^1$ is an alkyl of up to three carbon atoms, or allyl; $R^2$ is hydroxy (OH), chloro (Cl) or bromo (Br); and $R^3$ is hydrogen (H), an alkyl of up to four carbon atoms, allyl, or hydroxy (OH).

Examples of compounds represented by Formula I are:

A. Those in which A is

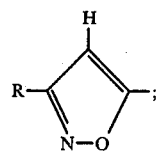

1. $R^1$ is allyl;
  a. $R^3$ is allyl;
    a.1. R is

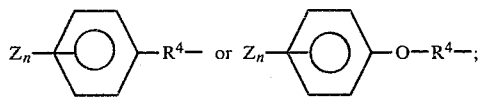

and $R^2$ is as defined herein.
3-[3-(1-(4-chlorophenyl)-1-methylethyl)-5-isoxazolyl]-1,5-di-(2-propen-1-yl)-4-hydroxy-2-imidazolidinone;
3-[3-(1-phenylethyl)-5-isoxazolyl]-1,5-di-(2-propen-1-yl)-4-hydroxy-2-imidazolidinone;
3-[3-(1-phenoxypropyl)5-isoxazolyl]-1,5-di-(2-propen-1-yl)-4-chloro-2-imidazolidinone;
3-[3-(1-(2,4-dichlorophenoxy)-1-methylethyl)-5-isoxazolyl]-1,5-di-(2-propen-1-yl)-4-hydroxy-2-imidazolidinone.

a.2. R is $-R^4-S-R^5$; and $R^2$ is as defined herein.
3-[3-(1-methyl-1-methylthioethyl)-5-isoxazolyl]-1,5-di-(2-propen-1-yl)-4-hydroxy-2-imidazolidinone;
3-[3-(1-methyl-1-(1-methylethylthio)ethyl)-5-isoxazolyl]-1,5-di-(2-propen-1-yl)-4-chloro-2-imidazolidinone.

a.3. R is $-R^4-O-R^5$; and $R^2$ is as defined herein.
3-[3-(1-methoxy-1-methylethyl)-5-isoxazolyl]-1,5-di-(2-propen-1-yl)-4-hydroxy-2-imidazolidinone;
3-[3-(1-ethoxy-1-methylbutyl)-5-isoxazolyl]-1,5-di-(2-propen-1-yl)-4-hydroxy-2-imidazolidinone.

a.4. R is a haloalkyl of up to six carbon atoms; and $R^2$ is as defined herein.
3-[3-(1-chloro-1-methylethyl)-5-isoxazolyl]-1,5-di-(2-propen-1-yl)-4-hydroxy-2-imidazolidinone;
3-[3-(1-chloromethyl-1-methylethyl-4-isoxazolyl]-1,5-di-(2-propen-1-yl)-4-hydroxy-2-imidazolidinone;
3-[3-(1-chloromethyl-1-ethylethyl)-5-isoxazolyl]-1,5-di-(2-propen-1-yl)-4-chloro-2-imidazolidinone.

a.5. R is trifluoromethyl ($-CF_3$); and $R^2$ is as defined herein.
3-(3-trifluoromethyl-5-isoxazolyl)-1,5-di-(2-propen-1-yl)-4-hydroxy-2-imidazolidinone;
3-(3-trifluoromethyl-5-isoxazolyl)-1,5-di-(2-propen-1-yl)-4-bromo-2-imidazolidinone.

a.6. R is a cycloalkyl as defined herein; and $R^2$ is as defined herein.
3-[3-cyclohexyl-5-isoxazolyl]-1,5-di-(2-propen-1-yl)-4-hydroxy-2-imidazolidinone;
3-[3-cyclopropyl-5-isoxazolyl]-1,5-di-(2-propen-1-yl)-4-hydroxy-2-imidazolidinone;
3-[3-cyclopentyl-5-isoxazolyl]-1,5-di-(2-propen-1-yl)-4-chloro-2-imidazolidinone.

a.7. R is an alkyl of up to six carbon atoms; and $R^2$ is as defined herein.
3-[3-(1-methylethyl)-5-isoxazolyl]-1,5-di-(2-propen-1-yl)-4-hydroxy-2-imidazolidinone;
3-[3-(1-ethyl-1-methylethyl)-5-isoxazolyl]-1,5-di-(2-propen-1-yl)-4-hydroxy-2-imidazolidinone.

a.8. R is tert-butyl, and $R^2$ is as defined herein.
3-[3-(1,1-dimethylethyl)-5-isoxazolyl]-1,5-di-(2-propen-1-yl)-4-hydroxy-2-imidazolidinone;
3-[3-(1,1-dimethylethyl)-5-isoxazolyl]-1,5-di-(2-propen-1-yl)-4-chloro-2-imidazolidinone.

a.9. R is an alkenyl or an alkynyl of up to five carbon atoms; and $R^2$ is as defined herein.
3-[3-(1,1-dimethyl-2-propyn-1-yl)-5-isoxazolyl]-1,5-di-(2-propen-1-yl)-4-hydroxy-2-imidazolidinone;
3-[3-(1,1-dimethyl-2-propen-1-yl)-5-isoxazolyl]-1,5-di-(2-propen-1-yl)-4-hydroxy-2-imidazolidinone.

b. $R^3$ is an alkyl of up to four carbon atoms;
    b.1.

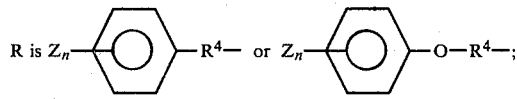

and $R^2$ is as defined herein.
3-[3-(1-(3,4-dimethylphenyl)-1-methylethyl)-5-isoxazolyl]-4-hydroxy-5-ethyl-1-(2-propen-1-yl)-2-imidazolidinone;
3-[3-(1-(2-chlorophenyl)-1-methylethyl)-5-isoxazolyl]-4-hydroxy-5-methyl-1-(2-propen-1-yl)-2-imidazolidinone.

b.2. R is $-R^4-S-R^5$; and $R^2$ is as defined herein.
3-[3-(1-methyl-1-methylthioethyl)-5-isoxazolyl]-4-hydroxy-5-methyl-1-(2-propen-1-yl)-2-imidazolidinone;
3-[3-(1-methylthioethyl)-5-isoxazolyl]-4-hydroxy-5-propyl-1-(2-propen-1-yl)-2-imidazolidinone.

b.3. R is $-R^4-O-R^5$; and $R^2$ is as defined herein.
3-[3-(1-methoxy-1-methylethyl)-5-isoxazolyl]-4-hydroxy-5-methyl-1-(2-propen-1-yl)-2-imidazolidinone;
3-[3-(1-methoxyethyl)-5-isoxazolyl]-4-chloro-5-ethyl-1-(2-propen-1-yl)-2-imidazolidinone.

b.4. R is a haloalkyl of up to six carbon atoms; and $R^2$ is as defined herein.
3-[3-(1-chloro-1-methylethyl)-5-isoxazolyl]-4-hydroxy-5-methyl-1-(2-propen-1-yl)-2-imidazolidinone;
3-[3-(1-chloromethyl-1-methylethyl)-5-isoxazolyl]-4-hydroxy-5-methyl-1-(2-propen-1-yl)-2-imidazolidinone.

b.5. R is trifluoromethyl ($-CF_3$); and $R^2$ is as defined herein.
(3-trifluoromethyl-5-isoxazolyl)-4-hydroxy-5-methyl-1-(2-propen-1-yl)-2-imidazolidinone;
3-(3-trifluoromethyl-5-isoxazolyl)-4-chloro-5-butyl-1-(2-propen-1-yl)-2-imidazolidinone.

b.6. R is a cycloalkyl as defined herein; and $R^2$ is as defined herein.
3-(3-cyclopropyl-5-isoxazolyl)-4-hydroxy-5-methyl-1-(2-propen-1-yl)-2-imidazolidinone;
3-(3-cyclohexyl-5-isoxazolyl)-4-hydroxy-5-butyl-1-(2-propen-1-yl)-2-imidazolidinone.

b.7. R is an alkyl of up to six carbon atoms; and $R^2$ is as defined herein.
3-[3-(1-methylethyl)-5-isoxazolyl]-4-hydroxy-5-methyl-1-(2-propen-1-yl)-2-imidazolidinone;
3-[3-(1-ethyl-1-methylethyl)-5-isoxazolyl]-4-hydroxy-5-methyl-1-(2-propen-1-yl)-2-imidazolidinone.

b.8. R is tert-butyl; and $R^2$ is as defined herein.
3-[3-(1,1-dimethylethyl)-5-isoxazolyl]-4-hydroxy-5-methyl-1-(2-propen-1-yl)-2-imidazolidinone;
3-[3-(1,1-dimethylethyl)-5-isoxazolyl]-4-chloro-5-methyl-1-(2-propen-1-yl)-2-imidazolidinone.

b.9. R is an alkenyl or an alkynyl of up to five carbon atoms; and $R^2$ is as defined herein.
3-[3-(1,1-dimethyl-2-propyn-1-yl)-5-isoxazolyl]-4-hydroxy-5-methyl-1-(2-propen-1-yl)-2-imidazolidinone;

3-[3-(1,1-dimethyl-2-propen-1-yl)-5-isoxazolyl]-4-hydroxy-5-methyl-1-(2-propen-1-yl)-2-imidazolidinone.

c. R$^3$ is hydrogen (H);
c.1. R is

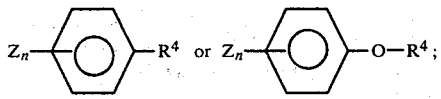

and R$^2$ is as defined herein.
3-[3-(1-phenoxy-1-methylethyl)-5-isoxazolyl]-4-hydroxy-1-(2-propen-1-yl)-2-imidazolidinone;
3-[3-(1-phenyl-1-methylethyl)-5-isoxazolyl]-4-hydroxy-1-(2-propen-1-yl)-2-imidazolidinone.

c.2. R is —R$^4$—S—R$^5$; and R$^2$ is as defined herein.
3-[3-(1-methyl-1-methylthioethyl)-5-isoxazolyl]-4-hydroxy-1-(2-propen-1-yl)-2-imidazolidinone;
3-[3-(1-methylthioethyl)-5-isoxazolyl]-4-hydroxy-1-(2-propen-1-yl)-2-imidazolidinone.

c.3. R is —R$^4$—O—R$^5$; and R$^2$ is as defined herein.
3-[3-(1-methoxy-1-methylethyl)-5-isoxazolyl]-4-hydroxy-1-(2-propen-1-yl)-2-imidazolidinone;
3-[3-(1-methoxyethyl)-5-isoxazolyl]-4-hydroxy-1-(2-propen-1-yl)-2-imidazolidinone.

c.4. R is a haloalkyl of up to six carbon atoms; and R$^2$ is as defined herein.
3-[3-(1-chloro-1-methylethyl)-5-isoxazolyl]-4-hydroxy-1-(2-propen-1-yl)-2-imidazolidinone;
3-[3-(1-chloromethyl-1-methylethyl)-5-isoxazolyl]-4-hydroxy-1-(2-propen-1-yl)-2-imidazolidinone.

c.5. R is trifluoromethyl (—CF$_3$); and R$^2$ is as defined herein.
3-(3-trifluoromethyl-5-isoxazolyl)-4-hydroxy-1-(2-propen-1-yl)-2-imidazolidinone.

c.6. R is a cycloalkyl as defined herein; and R$^2$ is as defined herein.
3-(3-cyclohexyl-5-isoxazolyl)-4-hydroxy-1-(2-propen-1-yl)-2-imidazolidinone;
3-(3-cyclopentyl-5-isoxazolyl)-4-chloro-1-(2-propen-1-yl)-2-imidazolidinone.

c.7. R is an alkyl of up to six carbon atoms; and R$^2$ is as defined herein.
3-[3-(1-methylethyl)-5-isoxazolyl]-4-hydroxy-1-(2-propen-1-yl)-2-imidazolidinone;
3-[3-(1-ethyl-1-methylethyl)-5-isoxazolyl]-4-hydroxy-1-(2-propen-1-yl)-2-imidazolidinone.

c.8. R is tert-butyl; and R$^2$ is as defined herein.
3-[3-(1,1-dimethylethyl)-5-isoxazolyl]-4-hydroxy-1-(2-propen-1-yl)-2-imidazolidinone;
3-[3-(1,1-dimethylethyl-5-isoxazolyl]-4-chloro-1-(2-propen-1-yl)-2-imidazolidinone.

c.9. R is an alkenyl or an alkynyl of up to five carbon atoms; and R$^2$ is as defined herein.
3-[3-(1,1-dimethyl-2-propyn-1-yl)-5-isoxazolyl]-4-hydroxy-1-(2-propen-1-yl)-2-imidazolidinone;
3-[3-(1,1-dimethyl-2-propen-1-yl)-5-isoxazolyl]-4-hydroxy-1-(2-propen-1-yl)-2-imidazolidinone.

d. R$^3$ is hydroxy (OH);
d.1. R is

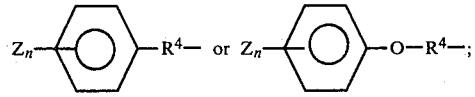

and R$^2$ is as defined herein.
3-[3-(1-phenoxy-1-methylethyl)-5-isoxazolyl]-4,5-dihydroxy-1-(2-propen-1-yl)-2-imidazolidinone;
3-[3-(1-phenylethyl)-5-isoxazolyl-4,5-dihydroxy-1-(2-propen-1-yl)-2-imidazolidinone.

d.2. R is —R$^4$—S—R$^5$; and R$^2$ is as defined herein.
3-[3-(1-methyl-1-methylthioethyl)-5-isoxazolyl]-4,5-dihydroxy-1-(2-propen-1-yl)-2-imidazolidinone;
3-[3-(1-methylthioethyl)-5-isoxazolyl]-4,5-dihydroxy-1-(2-propen-1-yl)-2-imidazolidinone.

d.3. R is —R$^4$—O—R$^5$; and R$^2$ is as defined herein.
3-[3-(1-methoxy-1-methylethyl)-5-isoxazolyl]-4,5-dihydroxy-1-(2-propen-1-yl)-2-imidazolidinone;
3-[3-(1-methoxyethyl)-5-isoxazolyl]-4,5-dihydroxy-1-(2-propen-1-yl)-2-imidazolidinone.

d.4. R is a haloalkyl of up to six carbon atoms; and R$^2$ is as defined herein.
3-[3-(1-chloro-1-methylethyl)-5-isoxazolyl]-4,5-dihydroxy-1-(2-propen-1-yl)-2-imidazolidinone;
3-[3-(1-chloromethyl-1-methylethyl)-5-isoxazolyl]-4,5-dihydroxy-1-(2-propen-1-yl)-2-imidazolidinone.

d.5. R is trifluoromethyl (—CF$_3$); and R$^2$ is as defined herein.
3-(3-trifluoromethyl-5-isoxazolyl)-4,5-dihydroxy-1-(2-propen-1-yl)-2-imidazolidinone;
3-(3-trifluoromethyl-5-isoxazolyl)-4-bromo-5-hydroxy-1-(2-propen-1-yl)-2-imidazolidinone.

d.6. R is a cycloalkyl as defined herein; and R$^2$ is as defined herein.
3-(3-cyclohexyl-5-isoxazolyl)-4,5-dihydroxy-1-(2-propen-1-yl)-2-imidazolidinone;
3-(3-cyclopropyl-5-isoxazolyl)-4,5-dihydroxy-1-(2-propen-1-yl)-2-imidazolidinone.

d.7. R is an alkyl of up to six carbon atoms; and R$^2$ is as defined herein.
3-[3-(1-methylethyl)-5-isoxazolyl]-4,5-dihydroxy-1-(2-propen-1-yl)-2-imidazolidinone;
3-[3-(1,1-dimethypropyl)-5-isoxazolyl]-4,5-dihydroxy-1-(2-propen-1-yl)-2-imidazolidinone.

d.8. R is tert-butyl; and R$^2$ is as defined herein.
3-[3-(1,1-dimethylethyl)-5-isoxazolyl]-4,5-dihydroxy-1-(2-propen-1-yl)-2-imidazolidinone;
3-[3-(1,1-dimethylethyl)-5-isoxazolyl]-4-chloro-5-hydroxy-1-(2-propen-1-yl)-2-imidazolidinone.

d.9. R is an alkenyl or an alkynyl of up to five carbon atoms; and R$^2$ is as defined herein.
3-[3-(1,1-dimethyl-2-propyn-1-yl)-5-isoxazolyl]-4,5-dihydroxy-1-(2-propen-1-yl)-2-imidazolidinone;
3-[3-(1,1-dimethyl-2-propen-1-yl)-5-isoxazolyl]-4,5-dihydroxy-1-(2-propen-1-yl)-2-imidazolidinone.

2. R$^1$ is an alkyl of up to three carbon atoms;
a R$^3$ is allyl;
a.1. R is

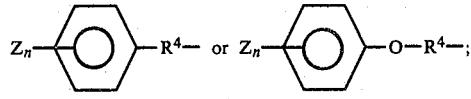

and $R^2$ is as defined herein.
3-[3-(1-phenyl-1-methylethyl)-5-isoxazolyl]-4-hydroxy-5-(2-propen-1-yl)-1-methyl-2-imidazolidinone;
3-[3-(1-phenoxyethyl)-5-isoxazolyl]-4-hydroxy-5-(2-propen-1-yl)-1-methyl-2-imidazolidinone.

a.2. R is $-R^4-S-R^5$; and $R^2$ is as defined herein.

3-[3-(1-methyl-1-methylthioethyl)-5-isoxazolyl]-4-hydroxy-5-(2-propen-1-yl)-1-methyl-2-imidazolidinone;
3-[3-(1-methylthioethyl)-5-isoxazolyl]-4-hydroxy-5-(2-propen-1-yl)-1-ethyl-2-imidazolidinone.

a.3. $R^1$ is $-R^4-O-R^5$; and $R^2$ is as defined herein.

3-[3-(1-methoxy-1-methylethyl)-5-isoxazolyl]-4-hydroxy-5-(2-propen-1-yl)-1-methyl-2-imidazolidinone;
3-[3-(1-methoxyethyl)-5-isoxazolyl]-4-hydroxy-5-(2-propen-1-yl)-1-methyl-2-imidazolidinone.

a.4. R is a haloalkyl of up to six carbon atoms; and $R^2$ is as defined herein.

3-[3-(1-chloro-1-methylethyl)-5-isoxazolyl]-4-hydroxy-5-(2-propen-1-yl)-1-propyl-2-imidazolidinone;
3-[3-(1-chloromethyl-1-methylethyl)-5-isoxazolyl]-4-hydroxy-1-methyl-5-(2-propen-1-yl)-2-imidazolidinone.

a.5. R is trifluoromethyl ($-CF_3$); and $R^2$ is as defined herein.

3-(3-trifluoromethyl-5-isoxazolyl)-4-hydroxy-5-(2-propen-1-yl)-1-methyl-2-imidazolidinone;
3-(3-trifluoromethyl-5-isoxazolyl)-4-hydroxy-5-(2-propen-1-yl)-1-ethyl-2-imidazolidinone.

a.6. R is a cycloalkyl as defined herein; and $R^2$ is as defined herein.

3-(3-cyclohexyl-5-isoxazolyl)-4-hydroxy-5-(2-propen-1-yl)-1-methyl-2-imidazolidinone;
3-(3-cyclopropyl-5-isoxazolyl)-4-chloro-5-(2-propen-1-yl)-1-methyl-2-imidazolidinone.

a.7. R is an alkyl of up to six carbon atoms; and $R^2$ is as defined herein.

3-[3-(1-methylethyl)-5-isoxazolyl]-4-hydroxy-5-(2-propen-1-yl)-1-ethyl-2-imidazolidinone;
3-[3-(1-methylpropyl)-5-isoxazolyl]-4-hydroxy-5-(2-propen-1-yl)-1-methyl-2imidazolidinone.

a.8. R is tert-butyl, and $R^2$ is as defined herein.

3-[3-(1,1-dimethylethyl)-5-isoxazolyl]-4-hydroxy-5-(2-propen-1-yl)-1-methyl-2-imidazolidinone;
3-[3-(1,1-dimethylethyl)-5-isoxazolyl]-4-chloro-5-(2-propen-1-yl)-1-propyl-2-imidazolidinone.

a.9. R is an alkenyl or an alkynyl of up to five carbon atoms; and $R^2$ is as defined herein.

3-[3-(1,1-dimethyl-2-propyn-1-yl)-5-isoxazolyl]-4-hydroxy-5-(2-propen-1-yl)-1-methyl-2-imidazolidinone;
3-[3-(1,2-dimethyl-1-propen-1-yl)-5-isoxazolyl]-4-hydroxy-5-(2-propen-1-yl)-1-methyl-2-imidazolidinone.

b. $R^3$ is an alkyl of up to four carbon atoms;
b.1. R is

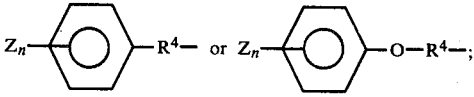

and $R^2$ is as defined herein.

3-[3-(1-(2,5-dichlorophenyl)-1-methylethyl)-5-isoxazolyl]-4-hydroxy-1,5-dimethyl-2-imidazolidinone;
3-[3-(1-(2,4-dimethylphenoxy)-1-methylethyl)-5-isoxazolyl]-4-hydroxy-5-ethyl-1-methyl-2-imidazolidinone.

b.2. R is $-R^4-S-R^5$; and $R^2$ is as defined herein.

3-[3-(1-methyl-1-methylthioethyl)-5-isoxazolyl]-4-hydroxy-1,5-dimethyl-2-imidazolidinone;
3-[3-(1-methylthioethyl)-5-isoxazolyl]-4-hydroxy-1,5-dimethyl-2-imidazolidinone.

b.3. R is $-R^4-O-R^5$; and $R^2$ is as defined herein.

3-[3-(1-methoxy-1-methylethyl)-5-isoxazolyl]-4-hydroxy-1,5-dimethyl-2-imidazolidinone;
3-[3-(1-methoxyethyl)-5-isoxazolyl]-4-hydroxy-1,5-dimethyl-2-imidazolidinone.

b.4. R is a haloalkyl of up to six carbon atoms; and $R^2$ is as defined herein.

3-[3-(1-chloro-1-methylethyl)-5-isoxazolyl]-4-hydroxy-1,5-dimethyl-2-imidazolidinone;
3-[3-(1-chloromethyl-1-methylethyl)-5-isoxazolyl]-4-hydroxy-1,5-dimethyl-2-imidazolidinone.

b.5. R is trifluoromethyl ($-CF_3$); and $R^2$ is as defined herein.

3-(3-trifluoromethyl-5-isoxazolyl)-4-hydroxy-1,5-dimethyl-2-imidazolidinone;
3-(3-trifluoromethyl-5-isoxazolyl)-4-hydroxy-5-ethyl-1-methyl-2-imidazolidinone.

b.6. R is a cycloalkyl as defined herein; and $R^2$ is as defined herein.

3-(3-cyclopropyl-5-isoxazolyl)-4-hydroxy-1,5-dimethyl-2-imidazolidinone;
3-(3-cyclohexyl-5-isoxazolyl)-4-hydroxy-1,5-dimethyl-2-imidazolidinone.

b.7. R is an alkyl of up to six carbon atoms; and $R^2$ is as defined herein.

3-[3-(1-methylethyl)-5-isoxazolyl]-4-hydroxy-1,5-dimethyl-2-imidazolidinone;
3-[3-(1-ethyl-1-methylethyl)-5-isoxazolyl]-4-hydroxy-1,5-dimethyl-2-imidazolidinone.

b.8. R is tert-butyl, and $R^2$ is as defined herein.

3-[3-(1,1-dimethylethyl)-5-isoxazolyl]-4-hydroxy-1,5-dimethyl-2-imidazolidinone;
3-[3-(1,1-dimethylethyl)-5-isoxazolyl]-4-hydroxy-1-methyl-5-ethyl-2-imidazolidinone.

b.9. R is an alkenyl or an alkynyl of up to five carbon atoms; and $R^2$ is as defined herein.

3-[3-(1,1-dimethyl-2-propyn-1-yl)-5-isoxazolyl]-4-hydroxy-1,5-dimethyl-2-imidazolidinone;
3-[3-(1,1-dimethyl-2-propen-1-yl)-5-isoxazolyl]-4-hydroxy-1,5-dimethyl-2-imidazolidinone.

c. $R^3$ is hydrogen (H);
c.1. R is

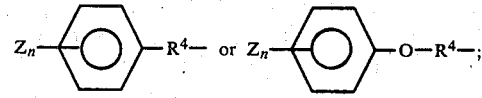

and $R^2$ is as defined herein.

3-[3-(1-phenyl-1-methylethyl)-5-isoxazolyl]-4-hydroxy-1-methyl-2-imidazolidinone;
3-[3-(1-(4-chlorophenoxy)-1-methylethyl)-5-isoxazolyl]-4-hydroxy-1-methyl-2-imidazolidinone.

c.2. R is $-R^4-S-R^5$; and $R^2$ is as defined herein.

3-[3-(1-methyl-1-methylthioethyl)-5-isoxazolyl]-4-hydroxy-1-methyl-2-imidazolidinone;
3-[3-(1-methylthioethyl)-5-isoxazolyl]-4-hydroxy-1-methyl-2-imidazolidinone.

c.3. R is —$R^4$—O—$R^5$; and $R^2$ is as defined herein.

3-[3-(1-methoxy-1-methylethyl)-5-isoxazolyl]-4-hydroxy-1-methyl-2-imidazolidinone;
3-[3-(1-methoxyethyl)-5-isoxazolyl]-4-hydroxy-1-methyl-2-imidazolidinone.

c.4. R is a haloalkyl of up to six carbon atoms; and $R^2$ is as defined herein.

3-[3-(1-chloro-1-methylethyl)-5-isoxazolyl]-4-hydroxy-1-methyl-2-imidazolidinone;
3-[3-(1-chloromethyl-1-methylethyl)-5-isoxazolyl]-4-hydroxy-1-methyl-2-imidazolidinone.

c.5. R is trifluoromethyl (—$CF_3$); and $R^2$ is as defined herein.

3-(3-trifluoromethyl-5-isoxazolyl)-4-hydroxy-1-methyl-2-imidazolidinone;
3-(3-trifluoromethyl-5-isoxazolyl)-4,5-dihydroxy-1-methyl-2-imidazolidinone.

c.6. R is a cycloalkyl as defined herein; and $R^2$ is as defined herein.

3-(3-cyclopropyl-5-isoxazolyl)-4-hydroxy-1-methyl-2-imidazolidinone;

c.7. R is an alkyl of up to six carbon atoms; and $R^2$ is as defined herein.

3-[3-(1,1-dimethylpropyl)-5-isoxazolyl]-4-hydroxy-1-methyl-2-imidazolidinone;
3-[3-(1,2-dimethylbutyl)-5-isoxazolyl]-4-hydroxy-1-methyl-2-imidazolidinone;
3-[3-(1-methylethyl)-5-isoxazolyl]-4-hydroxy-1-methyl-2-imidazolidinone.

c.8. R is tert-butyl; and $R^2$ is as defined herein.

3-[3-(1,1-dimethylethyl)-5-isoxazolyl]-4-hydroxy-1-methyl-2-imidazolidinone;
3-[3-(1,1-dimethylethyl)-5-isoxazolyl]-4-chloro-1-methyl-2-imidazolidinone.

c.9. R is an alkenyl or an alkynyl of up to five carbon atoms; and $R^2$ is as defined herein.

3-[3-(1,1-dimethyl-2-propyn-1-yl)-5-isoxazolyl]-4-hydroxy-1-methyl-2-imidazolidinone;
3-[3-(1,1-dimethyl-2-propen-1-yl)-5-isoxazolyl]-4-hydroxy-1-methyl-2-imidazolidinone.

d. $R^3$ is hydroxy (OH);
d.1. R is

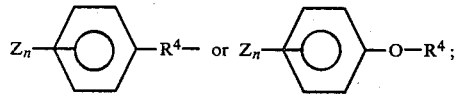

and $R^2$ is as defined herein.

3-[3-(1-phenyl-1-methylethyl)-5-isoxazolyl]-4,5-dihydroxy-1-methyl-2-imidazolidinone;
3-[3-(1-phenoxyethyl)-5-isoxazolyl]-4,5-dihydroxy-1-methyl-2-imidazolidinone.

d.2. R is —$R^4$—S—$R^5$; and $R^2$ is as defined herein.

3-[3-(1-methyl-1-methylthioethyl)-5-isoxazolyl]-4,5-dihydroxy-1-methyl-2-imidazolidinone;
3-[3-(1-methylthioethyl)-5-isoxazolyl]-4,5-dihydroxy-1-methyl-2-imidazolidinone.

d.3. R is —$R^4$—O—$R^5$; and $R^2$ is as defined herein.

3-[3-(1-methoxy-1-methylethyl)-5-isoxazolyl]-4,5-dihydroxy-1-methyl-2-imidazolidinone;
3-[3-(1-methoxyethyl)-5-isoxazolyl]-4,5-dihydroxy-1-methyl-2-imidazolidinone.

d.4. R is a haloalkyl of up to six carbon atoms; and $R^2$ is as defined herein.

3-[3-(1-chloro-1-methylethyl)-5-isoxazolyl]-4,5-dihydroxy-1-methyl-2-imidazolidinone;
3-[3-(1-chloromethyl-1-methylethyl)-5-isoxazolyl]-4,5-dihydroxy-1-methyl-2-imidazolidinone.

d.5. R is trifluoromethyl (—$CF_3$); and $R^2$ is as defined herein.

3-(3-trifluoromethyl-5-isoxazolyl)-4,5-dihydroxy-1-methyl-2-imidazolidinone;
3-(3-trifluoromethyl-5-isoxazolyl)-4-chloro-5-hydroxy-1-methyl-2-imidazolidinone.

d.6. R is a cycloalkyl as defined herein; and $R^2$ is as defined herein.

3-(3-cyclohexyl-5-isoxazolyl)-4,5-dihydroxy-1-methyl-2-imidazolidinone;
3-(3-cyclopropyl-5-isoxazolyl)-4,5-dihydroxy-1-methyl-2-imidazolidinone.

d.7. R is an alkyl of up to six carbon atoms; and $R^2$ is as defined herein.

3-[3-(1,1-dimethylpropyl)-5-isoxazolyl]-4,5-dihydroxy-1-methyl-2-imidazolidinone;
3-[3-(1-methylethyl)-5-isoxazolyl]-4,5-dihydroxy-1-methyl-2-imidazolidinone.

d.8. R is tert-butyl; and $R^2$ is as defined herein.

3-[3-(1,1-dimethylethyl)-5-isoxazolyl]-4,5-dihydroxy-1-methyl-2-imidazolidinone;
3-[3-(1,1-dimethylethyl)-5-isoxazolyl]-4-chloro-5-hydroxy-1-methyl-2-imidazolidinone.

d.9. R is an alkenyl or alkynyl of up to five carbon atoms; and $R^2$ is as defined herein.

3-[3-(1,1-dimethyl-2-propyn-1-yl)-5-isoxazolyl]-4,5-dihydroxy-1-methyl-2-imidazolidinone;
3-[3-(1,1-dimethyl-2-propen-1-yl)-5-isoxazolyl]-4,5-dihydroxy-1-methyl-2-imidazolidinone.

B. Those in which A is

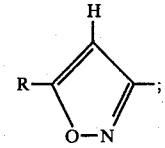

1. $R^1$ is allyl;
a. $R^3$ is allyl;
a.1. R is

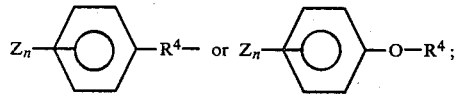

and $R^2$ is as defined herein.

3-[5-(1-phenyl-1-methylethyl)-3-isoxazolyl]-4-hydroxy-1,5-di-(2-propen-1-yl)-2-imidazolidinone;
3-[5-(1-(2-chlorophenoxy)-1-methylethyl)-3-isoxazolyl]-4-hydroxy-1,5-di-(2-propen-1-yl)-2-imidazolidinone.

a.2. R is —$R^4$—S—$R^5$; and $R^2$ is as defined herein.

3-[5-(1-methyl-1-methylthioethyl)-3-isoxazolyl]-4-hydroxy-1,5-di-(2-propen-1-yl)-2-imidazolidinone;

3-[5-(1-methylthioethyl)-3-isoxazolyl]-4-hydroxy-1,5-di-(2-propen-1-yl)-2-imidazolidinone.

a.3. R is —R⁴—O—R⁵; and R² is as defined herein.

3-[5-(1-methoxy-1-methylethyl)-3-isoxazolyl]-4-hydroxy-1,5-di-(2-propen-1-yl)-2-imidazolidinone;

3-[5-(1-methoxyethyl)-3-isoxazolyl]-4-hydroxy-1,1-di-(2-propen-1-yl)-2-imidazolidinone.

a.4. R is a haloalkyl of up to six carbon atoms; and R² is as defined herein.

3-[5-(1-chloro-1-methylpropyl)-3-isoxazolyl]-4-hydroxy-1,5-di-(2-propen-1-yl)-2-imidazolidinone;

3-[5-(1-chloromethyl-1-methylethyl)-3-isoxazolyl]-4-chloro-1,5-di-(2-propen-1-yl)-2-imidazolidinone.

a.5. R is trifluoromethyl (—CF₃); and R² is as defined herein.

3-(5-trifluoromethyl-3-isoxazolyl)-4-hydroxy-1,5-di-(2-propen-1-yl)-2-imidazolidinone;

3-(5-trifluoromethyl-3-isoxazolyl)-4-chloro-1,5-di-(2-propen-1-yl)-2-imidazolidinone.

a.6. R is a cycloalkyl as defined herein; and R² is as defined herein.

3-(5-cyclobutyl-3-isoxazolyl)-4-hydroxy-1,5-di-(2-propen-1-yl)-2-imidazolidinone;

3-(5-cyclohexyl-3-isoxazolyl)-4-hydroxy-1,5-di-(2-propen-1-yl)-2-imidazolidinone.

a.7. R is an alkyl of up to six carbon atoms; and R² is as defined herein.

3-[5-(1-methylbutyl)-3-isoxazolyl]-4-hydroxy-1,5-di-(2-propen-1-yl)-2-imidazolidinone;

3-[5-(1-methylethyl)-3-isoxazolyl]-4-hydroxy-1,5-di-(2-propen-1-yl)-2-imidazolidinone.

a.8. R is tert-butyl, and R² is as defined herein.

3-[5-(1,1-dimethylethyl)-3-isoxazolyl]-4-hydroxy-1,5-di-(2-propen-1-yl)-2-imidazolidinone;

3-[5-(1,1-dimethylethyl)-3-isoxazolyl]-4-chloro-1,5-di-(2-propen-1-yl)-2-imidazolidinone.

a.9. R is an alkenyl or an alkynyl of up to five carbon atoms; and R² is as defined herein.

3-[5-(1,1-dimethyl-2-propyn-1-yl)-3-isoxazolyl]-4-hydroxy-1,5-di-(2-propen-1-yl)-2-imidazolidinone;

3-[5-(1,1-dimethyl-2-propen-1-yl)-3-isoxazolyl]-4-hydroxy-1,5-di-(2-propen-1-yl)-2-imidazolidinone.

b. R³ is an alkyl of up to four carbon atoms;

b.1. R is

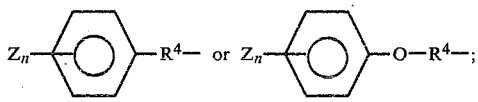

and R² is defined herein.

3-[5-(1-phenylpropyl)-3-isoxazolyl]-4-hydroxy-1-(2-propen-1-yl)-5-methyl-2-imidazolidinone.

3-[5-(1-(2-chlorophenoxy)-1-methylethyl)-3-isoxazolyl]-4-hydroxy-1-(2-propen-1-yl)-5-ethyl-2-imidazolidinone.

b.2. R is —R⁴—S—R⁵; and R² is as defined herein.

3-[5-(1-methyl-1-methylthioethyl)-3-isoxazolyl]-4-hydroxy-1-(2-propen-1-yl)-5-ethyl-2-imidazolidinone;

3-[5-(1-methylthioethyl)-3-isoxazolyl]-4-hydroxy-1-(2-propen-1-yl)-5-methyl-2-imidazolidinone.

b.3. R is —R⁴—O—R⁵; and R² is as defined herein.

3-[5-(1-methoxy-1-methylethyl)-3-isoxazolyl]-4-hydroxy-1-(2-propen-1-yl)-5-methyl-2-imidazolidinone;

3-[5-(1-methoxyethyl)-3-isoxazolyl]-4-hydroxy-1-(2-propen-1-yl)-5-ethyl-2-imidazolidinone.

b.4. R is a haloalkyl of up to six carbon atoms; and R² is as defined herein.

3-[5-(1-chloro-1-methylethyl)-3-isoxazolyl]-4-hydroxy-1-(2-propen-1-yl)-5-methyl-2-imidazolidinone;

3-[5-(1-chloromethyl-1-methylethyl)-3-isoxazolyl]-4-hydroxy-1-(2-propen-1-yl)-5-propyl-2-imidazolidinone.

b.5. R is trifluoromethyl (—CF₃); and R² is as defined herein.

3-(5-trifluoromethyl-3-isoxazolyl)-4-hydroxy-1-(2-propen-1-yl)-5-methyl-2-imidazolidinone;

3-(5-trifluoromethyl-3-isoxazolyl)-4-chloro-1-(2-propen-1-yl)-5-ethyl-2-imidazolidinone.

b.6. R is a cycloalkyl as defined herein; and R² is as defined herein.

3-(5-cyclohexyl-3-isoxazolyl)-4-hydroxy-1-(2-propen-1-yl)-5-methyl-2-imidazolidinone;

3-(5-cyclopropyl-3-isoxazolyl)-4-hydroxy-1-(2-propen-1-yl)-5-ethyl-2-imidazolidinone.

b.7. R is an alkyl of up to six carbon atoms; and R² is as defined herein.

3-[5-(1-methyl-1-ethylethyl)-3-isoxazolyl]-4-hydroxy-1-(2-propen-1-yl)-5-methyl-2-imidazolidinone;

3-[5-(1-methylethyl)-3-isoxazolyl]-4-hydroxy-1-(2-propen-1-yl)-5-methyl-2-imidazolidinone.

b.8. R is tert-butyl, and R² is as defined herein.

3-[5-(1,1-dimethylethyl)-3-isoxazolyl]-4-hydroxy-1-(2-propen-1-yl)-5-methyl-2-imidazolidinone;

3-[5-(1,1-dimethylethyl)-3-isoxazolyl]-4-hydroxy-1-(2-propen-1-yl)-5-ethyl-2-imidazolidinone.

b.9. R is an alkenyl or an alkynyl of up to five carbon atoms; and R² is as defined herein.

3-[5-(1,1-dimethyl-2-propyn-1-yl)-3-isoxazolyl]-4-hydroxy-1-(2-propen-1-yl)-5-methyl-2-imidazolidinone;

3-[5-(1,1-dimethyl-2-propen-1-yl)-3-isoxazolyl]-4-hydroxy-1-(2-propen-1-yl)-5-ethyl-2-imidazolidinone.

c. R³ is hydrogen (H);

c.1. R is

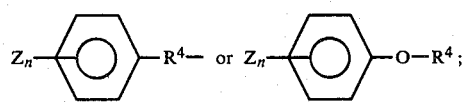

and R² is as defined herein.

3-[5-(1-(2-methylphenyl)-1-methylethyl)-3-isoxazolyl]-4-hydroxy-1-(2-propen-1-yl)-2-imidazolidinone;

3-[5-(1-phenoxy-1-methylethyl)-3-isoxazolyl]-4-hydroxy-1-(2-propen-1-yl)-2-imidazolidinone.

c.2. R is —R⁴—S—R⁵; and R² is as defined herein.

3-[5-(1-methyl-1-methylthiopropyl)-3-isoxazolyl]-4-hydroxy-1-(2-propen-1-yl)-2-imidazolidinone;

3-[5-(1-methylthioethyl)-3-isoxazolyl]-4-hydroxy-1-(2-propen-1-yl)-2-imidazolidinone.

c.3. R is —R⁴—O—R⁵; and R² is as defined herein.

3-[5-(1-methoxyethyl)-3-isoxazolyl]-4-hydroxy-1-(2-propen-1-yl)-2-imidazolidinone;

3-[5-(1-methoxy-1-methylpropyl)-3-isoxazolyl]-4-hydroxy-1-(2-propen-1-yl)-2-imidazolidinone.
  c.4. R is a haloalkyl of up to six carbon atoms; and R² is as defined herein.
3-[5-(1-chloro-1-methylbutyl)-3-isoxazolyl]-4-hydroxy-1-(2-propen-1-yl)-2-imidazolidinone;
3-[5-(1-chloro-1-ethylpropyl)-3-isoxazolyl]-4-hydroxy-1-(2-propen-1-yl)-2-imidazolidinone.
  c.5. R is trifluoromethyl (—CF₃); and R² is as defined herein.
3-(5-trifluoromethyl-3-isoxazolyl)-4-hydroxy-1-(2-propen-1-yl)-2-imidazolidinone;
3-(5-trifluoromethyl-3-isoxazolyl)-4-chloro-1-(2-propen-1-yl)-2-imidazolidinone.
  c.6. R is a cycloalkyl as defined herein; and R² is as defined herein.
3-(5-cyclopropyl-3-isoxazolyl)-4-hydroxy-1-(2-propen-1-yl)-2-imidazolidinone;
3-(5-cyclohexyl-3-isoxazolyl)-4-hydroxy-1-(2-propen-1-yl)-2-imidazolidinone.
  c.7. R is an alkyl of up to six carbon atoms; and R² is as defined herein.
3-[5-(1-methylethyl)-3-isoxazolyl]-4-hydroxy-1-(2-propen-1-yl)-2-imidazolidinone;
3-[5-(1-methyl-1-ethylethyl)-3-isoxazolyl]-4-hydroxy-1-(2propen-1-yl)-2-imidazolidinone.
  c.8. R is tert-butyl, and R² is as defined herein.
3-[5-(1,1-dimethylethyl)-3-isoxazolyl]-4-hydroxy-1-(2-propen-1-yl)-2-imidazolidinone;
3-[5-(1,1-dimethylethyl)-3-isoxazolyl]-4,5-dihydroxy-1-(2-propen-1-yl)-2-imidazolidinone.
  c.9. R is an alkenyl or an alkynyl of up to five carbon atoms; and R² is as defined herein.
3-[5-(1,1-dimethyl-2-propyn-1-yl)-3-isoxazolyl]-4-hydroxy-1-(2-propen-1yl)-2-imidazolidinone;
3-[5-(1,1-dimethyl-2-propen-1-yl)-3-isoxazolyl]-4-hydroxy-1-(2-propen-1-yl)-2-imidazolidinone.
 d. R³ is hydroxy (OH);
  d.1. R is

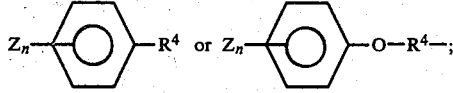

and R² is as defined herein.
3-[5-(1-phenyl-1-methylethyl)-3-isoxazolyl]-4,5-dihydroxy-1-(2-propen-1-yl)-2-imidazolidinone;
3-[5-(1-phenoxy-1-methylethyl)-3-isoxazolyl]-4,5-dihydroxy-1-(2-propen-1-yl)-2-imidazolidinone.
  d.2. R is —R⁴—S—R⁵; and R² is as defined herein.
3-[5-(1-methyl-1-methylthioethyl)-3-isoxazolyl]-4,5-dihydroxy-1-(2-propen-1-yl)-2-imidazolidinone;
3-[5-(1-methylthioethyl)-3-isoxazolyl]-4,5-dihydroxy-1-(2-propen-1-yl)-2-imidazolidinone.
  d.3. R is —R⁴—O—R⁵; and R² is as defined herein.
3-[5-(1-methoxy-1-methylethyl)-3-isoxazolyl]-4,5-dihydroxy-1-(2-propen-1-yl)-2-imidazolidinone;
3-[5-(1-methoxyethyl)-3-isoxazolyl]-4,5-dihydroxy-1-(2-propen-1-yl)-2-imidazolidinone.
  d.4. R is a haloalkyl of up to six carbon atoms; and R² is as defined herein.
3-[5-(1-chloro-1-methylethyl)-3-isoxazolyl]-4,5-dihydroxy-1-(2-propen-1-yl)-2-imidazolidinone;
3-[5-(1-chloromethyl-1-methylethyl)-3-isoxazolyl]-4,5-dihydroxy-1-(2-propen-1-yl)-2-imidazolidinone.
  d.5. R is trifluoromethyl (—CF₃); and R² is as defined herein.
3-(5-trifluoromethyl-3-isoxazolyl)-4,5-dihydroxy-1-(2-propen-1-yl)-2-imidazolidinone;
3-(5-trifluoromethyl-3-isoxazolyl)-4-chloro-5-hydroxy-1-(2-propen-1-yl)-2-imidazolidinone.
  d.6. R is a cycloalkyl as defined herein; and R² is as defined herein.
3-(5-cyclohexyl-3-isoxazolyl)-4,5-dihydroxy-1-(2-propen-1-yl)-2-imidazolidinone;
3-(5-cyclobutyl-3-isoxazolyl)-4,5-dihydroxy-1-(2-propen-1-yl)-2-imidazolidinone.
  d.7. R is an alkyl of up to six carbon atoms; and R² is as defined herein.
3-[5-(1-methylethyl)-3-isoxazolyl]-4,5-dihydroxy-1-(2-propen-1-yl)-2-imidazolidinone;
3-[5-(1,2-dimethylpropyl)-3-isoxazolyl]-4,5-dihydroxy-1-(2-propen-1-yl)-2-imidazolidinone.
  d.8. R is tert-butyl; and R² is as defined herein.
3-[5-(1,1-dimethylethyl)-3-isoxazolyl]-4,5-dihydroxy-1-(2-propen-1yl)-2-imidazolidinone;
3-[5-(1,1-dimethylethyl)-3-isoxazolyl]-4-chloro-5-hydroxy-1-(2-propen-1-yl)-2-imidazolidinone.
  d.9. R is an alkenyl or an alkynyl of up to five carbon atoms; and R² is as defined herein.
3-[5-(1,1-dimethyl-2-propyn-1-yl)-3-isoxazolyl]-4,5-dihydroxy-1-(2-propen-1-yl)-2-imidazolidinone;
3-[5-(1,1-dimethyl-2-propen-1-yl)-3-isoxazolyl]-4,5-dihydroxy-1-(2-propen-1-yl)-2-imidazolidinone.
2. R¹ is an alkyl of up to three carbon atoms;
 a. R³ is allyl;
  a.1. R is

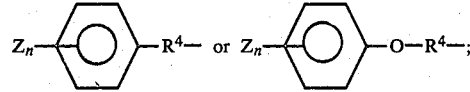

and R² is as defined herein.
3-[5-(1-phenylbutyl)-3-isoxazolyl]-4-hydroxy-1-methyl-5-(2-propen-1-yl)-2-imidazolidinone;
3-[5-(2-phenoxy-1-methylethyl)-3-isoxazolyl]-4-hydroxy-1-ethyl-5-(2-propen-1-yl)-2-imidazolidinone.
  a.2. R is —R⁴—S—R⁵; and R² is as defined herein.
3-[5(1-methyl-1-methylthioethyl)-3-isoxazolyl]-4-hydroxy-1-methyl-5-(2propen-1-yl)-2-imidazolidinone;
3[5-(1-methylthiopropyl)-3-isoxazolyl]-4-hydroxy-1-methyl-5-(2-propen-1-yl)-2-imidazolidinone.
  a.3. R is —R⁴—O—R⁵; and R² is as defined herein.
3-[5-(1-methoxyethyl)-3-isoxazolyl]-4-hydroxy-1-propyl-5-(2-propen-1-yl)-2-imidazolidinone;
3-[5-(1-methoxy-1-ethylethyl)-3-isoxazolyl]-4-hydroxy-1-ethyl-5-(2-propen-1-yl)-2-imidazolidinone.
  a.4. R is a haloalkyl of up to six carbon atoms; and R² is as defined herein.
3-[5-(1-chloro-1-methylpropyl)-3-isoxazolyl]-4-hydroxy-1-methyl-5-(2-propen-1-yl)-2-imidazolidinone;
3-[5-(2-chloro-1-methylbutyl)-3-isoxazolyl]-4-hydroxy-1-propyl-5-(2-propen-1-yl)-2-imidazolidinone.

a.5. R is trifluoromethyl (—CF₃); and R² is as defined herein.
3-(5-trifluoromethyl-3-isoxazolyl)-4-hydroxy-1-methyl-5-(2-propen-1-yl)-2-imidazolidinone;
3-(5-trifluoromethyl-3-isoxazolyl)-4-chloro-1-methyl-5-(2-propen-1-yl)-2-imidazolidinone.
  a.6. R is a cycloalkyl as defined herein; and R² is as defined herein.
3-(5-cyclopentyl-3-isoxazolyl)-4-hydroxy-1-methyl-5-(2-propen-1-yl)-2-imidazolidinone;
3-(5-cyclopropyl-3-isoxazolyl)-4-hydroxy-1-propyl-5-(2-propen-1-yl)-2-imidazolidinone.
  a.7. R is an alkyl of up to six carbon atoms; and R² is as defined herein.
3-[5-(1-methylethyl)-3-isoxazolyl]-4-hydroxy-1-methyl-5-(2-propen-1-yl)-2-imidazolidinone;
3-(5-methyl-3-isoxazolyl)-4-hydroxy-1-methyl-5-(2-propen-1-yl)-2-imidazolidinone.
  a.8. R is tert-butyl, and R² is as defined herein.
3-[5-(-1,1-dimethylethyl)-3-isoxazolyl]-4-hydroxy-1-methyl-5-(2-propen-1-yl)-2-imidazolidinone;
3-[5-(1,1-dimethylethyl)-3-isoxazolyl]-4-chloro-1-methyl-5-(2-propen-1-yl)-2-imidazolidinone.
  a.9. R is an alkenyl or an alkynyl of up to five carbon atoms; and R² is as defined herein.
3-[5-(1,1-dimethyl-2-propyn-1-yl)-3-isoxazolyl]-4-hydroxy-1-methyl-5-(2-propen-1-yl)-2-imidazolidinone;
3-[5-(1,1-dimethyl-2-propen-1yl)-3-isoxazolyl]-4-hydroxy-1-methyl-5-(2-propen-1-yl)-2-imidazolidinone.
 b. R³ is an alkyl of up to four carbon atoms;
  b.1. R is

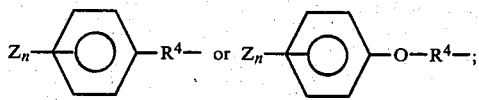

and R² is as defined herein.
3-[5-(1-phenoxypropyl)-3-isoxazolyl]-4-hydroxy-1,5-dimethyl-2-imidazolidinone;
3-[5-(2-phenyl-1-methylethyl)-3-isoxazolyl]-4-hydroxy-1,5-diethyl-2-imidazolidinone.
  b.2. R is —R⁴—S—R⁵; and R² is as defined herein.
3-[5-(1-methylthioethyl)-3-isoxazolyl]-4-hydroxy-1-methyl-5-propyl-2-imidazolidinone;
3-[5-(1-methyl-1-methylthioethyl)-3-isoxazolyl]-4-hydroxy-1-ethyl-5-methyl-2-imidazolidinone.
  b.3. R is —R⁴—O—R⁵; and R² is as defined herein.
3-[5-(1-methoxyethyl)-3-isoxazolyl]-4-chloro-1,5-dimethyl-2-imidazolidinone;
3-[5-(1-methoxy-1-methylpropyl)-3-isoxazolyl]-4-hydroxy-1,5-dimethyl-2-imidazolidinone.
  b.4. R is a haloalkyl of up to six carbon atoms; and R² is as defined herein.
3-[5-(1-chloro-1-methylbutyl)-3-isoxazolyl]-4-hydroxy-1,5-dimethyl-2-imidazolidinone;
3-[5-(1-chloromethyl-1-methylethyl)-3-isoxazolyl]-4-hydroxy-1,5-dimethyl-2-imidazolidinone.
  b.5. R is trifluoromethyl (—CF₃); and R² is as defined herein.
3-(5-trifluoromethyl-3-isoxazolyl)-4-hydroxy-1,5-dimethyl-2-imidazolidinone;
3-(5-trifluoromethyl-3-isoxazolyl)-4-chloro-1,5-dimethyl-2-imidazolidinone.
  b.6. R is a cycloalkyl as defined herein; and R² is as defined herein.
3-(5-cyclohexyl-3-isoxazolyl)-4-hydroxy-1,5-dimethyl-2-imidazolidinone;
3-(5-cyclopentyl-3-isoxazolyl)-4-hydroxy-1,5-dimethyl-2-imidazolidinone.
  b.7. R is an alkyl of up to six carbon atoms; and R² is as defined herein.
3-[5-(1-ethylethyl)-3-isoxazolyl]-4-hydroxy-1,5-dimethyl-2-imidazolidinone;
3-[5-(1-methylethyl)-3-isoxazolyl]-4-hydroxy-1,5-dimethyl-2-imidazolidinone.
  b.8. R is tert-butyl; and R² is as defined herein.
3-[5-(1,1-dimethylethyl)-3-isoxazolyl]-4-hydroxy-1,5-dimethyl-2-imidazolidinone;
3-[5-(1,1-dimethylethyl)-3-isoxazolyl]-4-hydroxy-1,5-dimethyl-2-imidazolidinone.
  b.9. R is an alkenyl or an alkynyl of up to five carbon atoms; and R² is as defined herein.
3-[5-(1,1-dimethyl-2-propyn-1-yl)-3-isoxazolyl]-4-hydroxy-1-ethyl-5-methyl-2-imidazolidinone;
3-[5-(1,1-dimethyl-2-propen-1-yl)-3-isoxazolyl]-4-hydroxy-1,5-dimethyl-2-imidazolidinone.
 c. R³ is hydrogen (H);
  c.1. R is

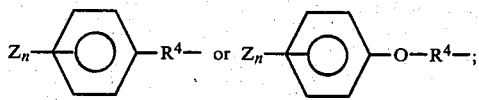

and R² is as defined herein.
3-[5-(1-phenylethyl)-3-isoxazolyl]-4-hydroxy-1-methyl-2-imidazolidinone;
3-[5-(2-(2-chlorophenyl)-1-methylethyl)-3-isoxazolyl]-4-hydroxy-1-methyl-2-imidazolidinone.
  c.2. R is —R⁴—S—R⁵; and R² is as defined herein.
3-[5-(1-methylthioethyl)-3-isoxazolyl]-4-hydroxy-1-ethyl-2-imidazolidinone;
3-[5-(1-methyl-1-methylthioethyl)-3-isoxazolyl]-4-hydroxy-1-methyl-2-imidazolidinone.
  c.3. R is —R⁴—O—R⁵; and R² is as defined herein.
3-[5-(1-methoxyethyl)-3-isoxazolyl]-4-hydroxy-1-ethyl-2-imidazolidinone;
3-[5-(1-methoxy-1-methylethyl)-3-isoxazolyl]-4-hydroxy-1-methyl-2-imidazolidinone.
  c.4. R is a haloalkyl of up to six carbon atoms; and R² is as defined herein.
3-[5-(1-chloro-1-methylethyl)-3-isoxazolyl]-4-hydroxy-1-methyl-2-imidazolidinone;
3-[5-(1-chloromethyl-1-methylethyl)-3-isoxazolyl]-4-hydroxy-1-methyl-2-imidazolidinone.
  c.5. R is trifluoromethyl(—CF₃); and R² is as defined herein.
3-(5-trifluoromethyl-3-isoxazolyl)-4-hydroxy-1-methyl-2-imidazolidinone;
3-(5-trifluoromethyl-3-isoxazolyl)-4-chloro-1-methyl-2-imidazolidinone.
  c.6. R is a cycloalkyl as defined herein; and R² is as defined herein.
3-(5-cyclohexyl-3-isoxazolyl)-4-hydroxy-1-methyl-2-imidazolidinone;

3-(5-cyclopropyl-3-isoxazolyl)-4-hydroxy-1-methyl-2-imidazolidinone.

c.7. R is an alkyl of up to six carbon atoms; and R² is as defined herein.

3-[5-(1-methylethyl)-3-isoxazolyl]-4-hydroxy-1-methyl-2-imidazolidinone;

3-[5-(1,1-dimethylpropyl)-3-isoxazolyl]-4-hydroxy-1-methyl-2-imidazolidinone.

c.8. R is tert-butyl, and R² is as defined herein.

3-[5-(1,1-dimethylethyl)-3-isoxazolyl]-4-hydroxy-1-methyl-2-imidazolidinone;

3-[5-(1,1-dimethylethyl)-3-isoxazolyl]-4-chloro-1-methyl-2-imidazolidinone.

c.9. R is an alkenyl or an alkynyl of up to five carbon atoms; and R² is as defined herein.

3-[5-(1,1-dimethyl-2-propyn-1-yl)-3-isoxazolyl]-4-hydroxy-1-methyl-2-imidazolidinone;

3-[5-(1,1-dimethyl-2-propen-1-yl)-3-isoxazolyl]-4-hydroxy-1-methyl-2-imidazolidinone.

d. R³ is hydroxy (OH);

d.1. R is

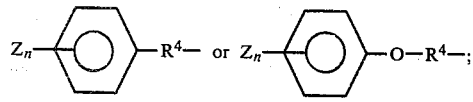

and R² is as defined herein.

3-[5-(1-phenyl-1-methylethyl)-3-isoxazolyl]-4,5-dihydroxy-1-methyl-2-imidazolidinone;

3-[5-(1-phenoxy-1-methylethyl)-3-isoxazolyl]-4,5-dihydroxy-1-methyl-2-imidazolidinone.

d.2. R is —R⁴—S—R⁵; and R² is as defined herein.

3-[5-(1-methyl-1-methylthioethyl)-3-isoxazolyl]-4,5-dihydroxy-1-methyl-2-imidazolidinone;

3-[5-(1-methylthioethyl)-3-isoxazolyl]-4,5-dihydroxy-1-methyl-2-imidazolidinone.

d.3. R is —R⁴—O—R⁵; and R² is as defined herein.

3-[5-(1-methoxy-1-methylethyl)-3-isoxazolyl]-4,5-dihydroxy-1-methyl-2-imidazolidinone;

3-[5-(1-methoxyethyl)-3-isoxazolyl]-4,5-dihydroxy-1-methyl-2-imidazolidinone.

d.4. R is a haloalkyl of up to six carbon atoms; and R² is as defined herein.

3-[5-(1-chloro-1-methylethyl)-3-isoxazolyl]-4,5-dihydroxy-1-methyl-2-imidazolidinone;

3-[5-(1-chloromethyl-1-methylethyl)-3-isoxazolyl]-4,5-dihydroxy-1-methyl2-imidazolidinone.

d.5. R is trifluoromethyl; and R² is as defined herein.

3-(5-trifluoromethyl-3-isoxazolyl)-4,5-dihydroxy-1-methyl-2-imidazolidinone;

3-(5-trifluoromethyl-3-isoxazolyl)-4-chloro-5-hydroxy-1-methyl-2-imidazolidinone.

d.6. R is a cycloalkyl as defined herein; and R² is as defined herein.

3-(5-cyclohexyl-3-isoxazolyl)-4,5-dihydroxy-1-methyl-2-imidazolidinone;

3-(5-cyclopentyl-3-isoxazolyl)-4,5-dihydroxy-1-methyl-2-imidazolidinone.

d.7. R is an alkyl of up to six carbon atoms; and R² is as defined herein.

3-[5-(1-methylethyl)-3-isoxazolyl]-4,5-dihydroxy-1-methyl-2-imidazolidinone;

3-[5-(1,1-dimethylpropyl)-3-isoxazolyl]-4,5-dihydroxy-1-methyl-2-imidazolidinone.

d.8. R is tert-butyl; and R² is as defined herein.

3-[5-(1,1-dimethylethyl)-3-isoxazolyl]-4,5-dihydroxy-1-methyl-2-imidazolidinone;

3-[5-(1,1-dimethylethyl-3-isoxazolyl]-4-chloro-1-methyl-5-hydroxy-2-imidazolidinone.

d.9. R is an alkenyl or an alkynyl of up to five carbon atoms; and R² is as defined herein.

3-[5-(1,1-dimethyl-2-propyn-1-yl)-3-isoxazolyl]-4,5-dihydroxy-1-methyl-2-imidazolidinone;

3-[5-(1,1-dimethyl-2-propen-1-yl)-3-isoxazolyl]-4,5-dihydroxy-1-methyl-2-imidazolidinone.

In the compounds described herein, some compounds are more preferred than others for the uses described herein. Thus, in those compounds where R¹ is an alkyl, the order of preference is as follows: methyl is preferred over the straight alkyls, which are preferred over the branched alkyls. As to R, branched alkyls are preferred over the straight alkyls, which are preferred over methyl. When R is a cycloalkyl, the preferred order of preference is cyclohexyl, followed by cyclopentyl, cyclobutyl, and cyclopropyl. When R is a haloalkyl of up to six carbon atoms, the most preferred haloalkyl is trifluoromethyl (CF₃), followed by the branched haloalkyls, preferably the halo for the haloalkyl is chlorine (Cl), and generally the monochloronated haloalkyls are preferred. When R² is as described herein, it is preferred that R² be hydroxy and next preferred is chlorine and bromine. When R³ is as described herein, it is preferred that it be hydrogen, followed by hydroxy (OH), methyl, an alkyl, and allyl.

Preferred compounds have R² as hydroxy (OH).

Highly preferred compounds have R² as hydroxy, and R³ as methyl, hydroxy, or hydrogen, with hydrogen being preferred.

Very highly preferred compounds have R² as hydroxy; R³ as methyl, hydroxy, or hydrogen, with hydrogen being preferred; and R¹ as methyl.

The preferred compounds, highly preferred compounds, and very highly preferred compounds which have R as 1,1-dimethylethyl (t-butyl), 1-methylethyl (isopropyl), or trifluoromethyl are especially preferred.

In general, of all the compounds described herein, it is preferred that A be

Examples of the most preferred compounds described herein are given in descending order of preference:

3-[5-(1,1-dimethylethyl)-3-isoxazolyl]-4-hydroxy-1-methyl-2-imidazolidinone;

3-[5-(1,1-dimethylethyl)-3-isoxazolyl]-4,5-dihydroxy-1-methyl-2-imidazolidinone;

3-[5-(1-methylethyl)-3-isoxazolyl]-4-hydroxy-1-methyl-2-imidazolidinone;

3-[5-(1-methylethyl)-3-isoxazolyl]-4,5-dihydroxy-1-methyl-2-imidazolidinone;

3-(5-trifluoromethyl-3-isoxazolyl)-4-hydroxy-1-methyl-2-imidazolidinone;

3-(5-trifluoromethyl-3-isoxazolyl)-4,5-dihydroxy-1-methyl-2-imidazolidinone;

3-[5-(1,1-dimethylethyl)-3-isoxazolyl]-4-hydroxy-1,5-dimethyl-2-imidazolidinone;
3-[5-(1-methylethyl)-3-isoxazolyl]-4-hydroxy-1,5-dimethyl-2-imidazolidinone;
3-(5-trifluoromethyl-3-isoxazolyl)-4-hydroxyl-1,5-dimethyl-2-imidazolidinone;
3-[3-(1,1-dimethylethyl)-5-isoxazolyl]-4-hydroxy-1-methyl-2-imidazolidinone;
3-[3-(1,1-dimethylethyl)-5-isoxazolyl]-4,5-dihydroxy-1-methyl-2-imidazolidinone;
3-[3-(1-methylethyl)-5-isoxazolyl]-4-hydroxy-1-methyl-2-imidazolidinone;
3-[3-(1-methylethyl)-5-isoxazolyl]-4,5-dihydroxy-1-methyl-2-imidazolidinone;
3-(3-trifluoromethyl-5-isoxazolyl)-4-hydroxy-1-methyl-2-imidazolidinone;
3-(3-trifluoromethyl-5-isoxazolyl)-4,5-dihydroxy-1-methyl-2-imidazolidinone;
3[3-(1,1-dimethylethyl)-5-isoxazolyl]-4-hydroxy-1,5-dimethyl-2-imidazolidinone;
3-[3-(1-methylethyl)-5-isoxazolyl]-4-hydroxy-1,5-dimethyl-2-imidazolidinone;
3-(3-trifluoromethyl-5-isoxazolyl)-4-hydroxy-1,5-dimethyl-2-imidazolidinone.

SYNTHESIS OF THE COMPOUNDS

1. General Synthesis of Compounds of Formula I where $R^2$ is hydroxy (OH) and $R^3$ is not hydroxy (OH).

The synthesis of the compounds described herein, wherein $R^2$ is OH and $R^3$ is not OH, proceeds according to the general reactions 1, 2, and 3 shown below:

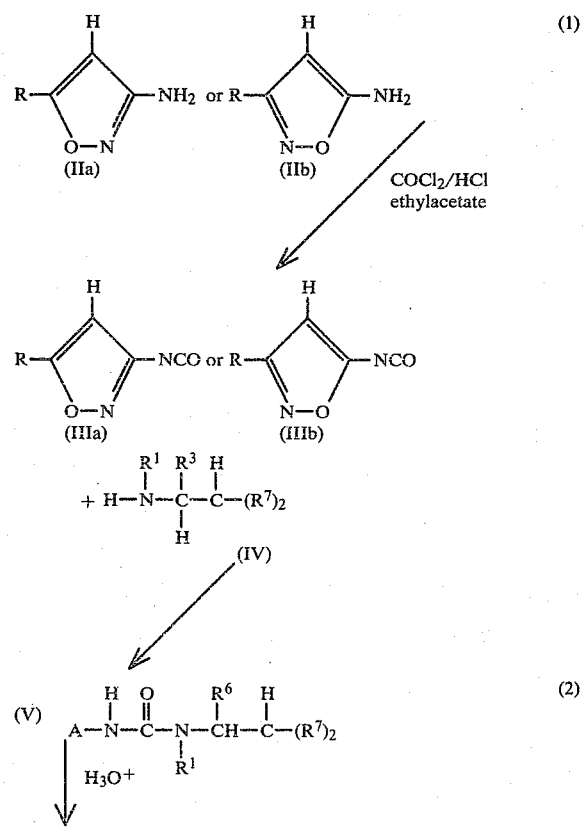

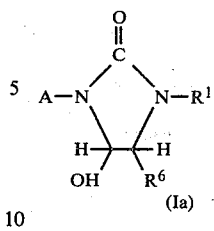

Preparation of the Isocyanate

Five to 10 grams of the appropriate 5-substituted-3-aminoisoxazole (IIa) or 3-substituted-5-aminoisoxazole (graphically represented by Formulas IIa and IIb respectively), wherein R is as defined herein, is reacted (reaction 1) by adding it to a solution of phosgene and HCl in ethylacetate (or other suitable solvent) prepared by adding an excess of gaseous HCl to 50–100 milliliters of solvent, saturating this solution with phosgene at room temperature, and then adding another 50–100 milliliters of solvent. The mixture is allowed to react while stirring overnight at room temperature and is then purged with nitrogen or argon to remove the unreacted phosgene. In those cases where a solid was obtained, the product (graphically represented by Formulas IIIa or IIIb, which is an isocyanate of the appropriately substituted isoxazole) was isolated by filtration and dried. In cases where no solid product is evident, the reaction mixture may be topped under vacuum to give the product as a viscous oil or glass.

Note, the appropriate isoxazole of Formula II may be obtained from commercial sources or made by any of the methods known in the art.

Preparation of Acetal Ureas

The appropriate isocyanate of Formula IIIa or IIIb is reacted with an equivalent amount of substituted amino-substituted-acetaldehyde dialkylacetal represented by Formula IV, where $R^1$ is as defined herein; $R^6$ is like $R^3$ but is not hydroxy, that is, $R^6$ is hydrogen, an alkyl of up to four carbon atoms, or allyl; and $R^7$ is an alkoxy of up to six carbon atoms, but preferably methoxy, an alkylthio of up to six carbon atoms, or a moiety reactive with the hydrogen atom attached to the nitrogen atom nearest the ring whereby a cyclic structure of Formula I forms under cyclization reactions. The compounds are heated to reflux (2–15 minutes) in an inert solvent such as ether, benzene, toluene, or ethylacetate, etc., and the reaction proceeds as shown by reaction equation (2) so as to form the urea product graphically represented by Formula V, where A, $R^1$, $R^6$, and $R^5$ are as defined herein. Some products may be produced as crystals directly from solution, but others may be induced by the addition of hexane. If no solid forms, the solvent is removed by distillation, evaporation, or other technique to yield the crude product as an oil or solid. The product represented by graphic Formula V may be purified chromatographically, by washing with ether or hexane, or recrystallized from hexane/benzene or from ether/benzene or from ether/chloroform/benzene solutions, or by other methods known in the art.

Note: The appropriate alkylamino-substituted-acetaldehyde dimethylacetal represented by Formula IV may be obtained from commercial sources or made by any of the methods known in the art. Further other acetals such as ethyl may be used, but methyl is preferred.

Preparation of the Compounds of Formula Ia

The appropriate acetal urea of Formula V (approximately three to four grams) is added to 150-200 milliliters of water containing 1.5-2 milliliters of concentrated hydrochloric acid. The mixture is stirred vigorously and heated to reflux and reaction proceeds as shown by reaction equation (3). The hydrolysis is monitored by thin layer chromatography (alumina-ethylacetate) until complete and the product forms. The product, represented by Formula Ia, where A, $R^1$ and $R^6$ are as defined herein, in some cases may be crystallized directly from the reaction mixture upon cooling. In other cases, the compounds of Formula Ia are extracted with chloroform and isolated by stripping the solvent under vacuum. Those compounds which solidify upon concentration are further purified. In some cases, the compounds may be used directly as obtained. In other cases, crystallization is induced by seeding an ether solution with a related compound, and the crystals formed may be further purified.

2. General synthesis of compounds of Formula I where $R^2$ and $R^3$ are both hydroxy (OH)

Compounds represented by Formula I where $R^2$ and $R^3$ are both hydroxide, as represented by Formula Ib, where A and $R^1$ are as defined herein:

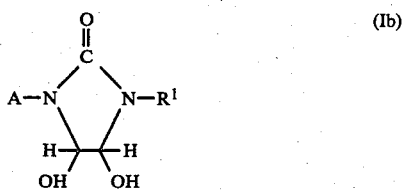

are synthesized according to reaction equations 4 and 5.

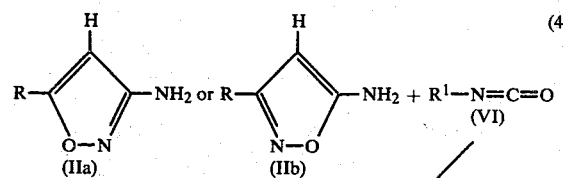

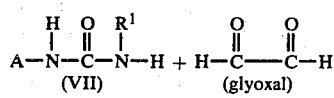

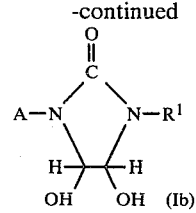

Preparation of the Ureas Represented by Formula VII

The appropriate isoxazol amine represented by Formula IIa or IIb is reacted with the appropriate isocyanate of Formula VI where $R^1$ is as defined herein, in an inert solvent, such as benzene, ether, or toluene, with a small amount of alkylamine catalyst such as triethylamine at temperatures from about 15° C. to the reflux temperature of the mixture (reaction 4). The urea of Formula VII is generally separated from the reaction mixture by any of the techniques known in the art.

Preparation of the 4,5-dihydroxy-substituted-imidazolidinone Represented by Formula Ib The appropriate urea of Formula VII is reacted with a 40 percent aqueous glyoxal solution which has been adjusted to a pH of 7.0-8.0 with a suitable base such as aqueous sodium hydroxide at temperatures from 15° C. to 80° C., but preferably from 20° C. to 40° C., over a period of from ten (10) hours to up to 132 hours. The product (a compound of Formula Ib) is separated by any of the techniques known in the art.

3. General synthesis of the compounds of Formula I where $R^2$ is bromo (Br) or chloro (Cl)

Those compounds represented by Formula I in which $R^2$ is bromo or chloro are prepared from compounds represented by Formulas Ia and Ib by reaction with about 10 percent excess of a halogenating agent (for example, thionyl chloride, phosphorus oxychloride, phosphorous trichloride, or phosphorous pentachloride), optionally in the presence of a diluent (e.g. benzene, toluene, methylene chloride, etc.), and optionally in the presence of an acid binding agent (such as an organic base, alkali metal hydroxide, or carbonate), but preferably, without the addition of an acid binder; and the acid formed is removed by concentration, hydrolysis, or distillation. When compounds represented by Formula Ib are used, it is necessary to protect the hydroxy at the $R^3$ position by any of the known techniques used in synthesis reactions, such as alkylation, followed by removal of the alkyl group.

The following examples illustrate the synthesis of the compounds described herein.

EXAMPLE I

Synthesis of 3-[5-(1,1-dimethylethyl)-3-isoxazolyl]-1-methyl-4-hydroxy-2-imidazolidinone a. Formation of 5-(1,1-dimethylethyl)isoxazol-3-yl isocyanate A 300 milliliter, 3-neck flask equipped with a magnetic stirrer, thermometer, and dry ice condenser/drying tube was charged with 100 milliliters of ethylacetate solution containing 4.8 grams (0.034 mole) of 3-amino-5-(1,1-dimethylethyl)isoxazole. Anhydrous hydrochloric acid gas (10.0 grams) was bubbled into the solution, and then 20 grams of phosgene was bubbled into the solution, which was cooled in an ice bath. The solution was allowed to stand at ambient temperature for 17 hours and then the flask was purged with argon until no $COCl_2$ was detected. The solution was filtered under nitrogen, and the precipitate was washed with benzene to give a precipitate containing about 0.034 mole (5.6 grams) of 5-(1,1-dimethylethyl)isoxazol-3-yl isocyanate.

b. Formation of 3-[5-(1,1-dimethylethyl-3-isoxazolyl]-1-methyl-1-(2,2-dimethoxyethyl)urea At ambient temperatures, 4.2 grams (0.035 mole) of methylaminoacetaldehyde dimethylacetal in 15 milliliters of benzene was rapidly added to 50 milliliters of benzene solution containing 0.034 mole (5.6 grams) of the precipitate of 5-(1,1-dimethylethyl)isoxazolyl-3-yl isocyanate (prepared above). The resulting slurry was heated to reflux for two (2) minutes, filtered, cooled, and 20 milliliters of hexane added, but no crystals formed upon standing and cooling in a refrigerator. It was then topped on a roto-vac at 70° C. to yield 5.7 grams of a viscous oil containing 3-[5-(1,1-dimethylethyl)-3-isoxazolyl]-1-methyl-1-(2,2-dimethoxyethyl)urea. The oil crystallized on cooling, and the crystals were recrystallized from ethyl ether/hexane solution with refrigeration. The crystals were removed by suction filtration and air dried to yield 5.2 grams of white crystals of 3-[5-(1,1-dimethylethyl)-3-isoxazolyl]-1-methyl-1-(2,2-dimethoxyethyl)urea. M.P. 80°–84° C., IR spectra (mull.) bands at 3260, 1670, 1600, and 1530 $cm^{-1}$, MS ion at m/e at 285.

NMR ($CDCl_3$) 9.11$\delta$ (singlet, 1H); 6.61$\delta$ (singlet, 1H); 4.52$\delta$ (triplet, 1H); 3.42$\delta$ (singlet, 8H); 3.50$\delta$ (doublet, 8H); 3.13$\delta$ (singlet, 3H); 1.30$\delta$ (singlet, 9H).

c. Synthesis of 3-[5-(1,1-dimethylethyl)-3-isoxazolyl]-1-methyl-4-hydroxy-2-imidazolidinone A round bottom flask was charged with 2.6 grams of the 3-[5-(1,1-dimethylethyl)-3-isoxazoly]-1-methyl-(2,2-dimethoxyethyl)urea (prepared above), 150 milliliters of water and 1.5 milliliters of concentrated hydrochloric acid (HCl). The resulting mixture was heated until one phase formed, and crystals coated out on the sides of the flask and cooled; and the scrapings of the crystals and the solution were filtered. The crystalline precipitate was washed twice with separate portions of $H_2O$, and then air dried to yield 1.9 grams of white crystals of 3-[5-(1,1-dimethylethyl)-3-isoxazolyl]-1-methyl-4-hydroxy-2-imidazolidinone. M.P. 173°–177° C., IR spectra (mull.) bands at 3400, 3140, 1700, and 1590 $cm^{-1}$.

NMR ($CDCl_3$): 6.64$\delta$ (singlet, 1H); 5.83$\delta$ (multiplet, 1H); 4.92$\delta$ (broad singlet, 1H); 3.83–3.17$\delta$ (multiplet, 2H); 2.89$\delta$ (singlet, 3H); 1.30$\delta$ (singlet, 9H).

EXAMPLE II

Synthesis of 3-[3-(1,1-dimethylethyl)-5-isoxazolyl]-4,5-dihydroxy-1-methyl-2-imidazolidinone a. Formation of 1-[3-(1,1-dimethylethyl)-5-isoxazolyl]-3-methylurea

A 50 milliliter flask with a magnetic stirring bar was charged with 1.3 grams (0.0093 mole) of 3-(1,1-dimethylethyl)-5-isoxazolamine and 25 milliliters of benzene. To this was added 1.7 grams of methyl isocyanate and one (1) drop of triethylamine; and the mixture was allowed to stand overnight, after which it was heated to reflux for 7.5 hours and then allowed to stand at room temperature for two (2) days. Thin layer chromatography showed only partial reaction, so a trace of 4-dimethylaminopyridine and several milliliters of methyl isocyanate were added and the mixture heated at reflux for 4.5 hours. The mixture was then concentrated on a rotary evaporator to give 2.6 grams of a viscous red brown oil. Chromatography on alumina with chloroform/ethyl acetate monitored by TLC gave fractions containing a single component. These fractions were combined and evaporated to give 0.67 gram of a pale yellow solid of 1-[3-(1,1-dimethylethyl)-5-isoxazolyl]-3-methylurea, M.P. 188°–196° C., which showed a molecular ion at 197 in the mass spectrum.

b. Formation of 3-[3-(1,1-dimethylethyl)-5-isoxazolyl]-4,5-dihydroxy-1-methyl-2-imidazolidinone The 0.67 gram (0.0034 mole) of 1-[3-(1,1-dimethylethyl)-5-isoxazolyl]-3-methylurea prepared above was dissolved in 5 milliliters of ethanol. To this was added 1.5 grams of a 40 percent aqueous glyoxal solution previously adjusted to pH 7 with dilute sodium hydroxide solution. After standing at room temperature for 2.5 days, the mixture was topped on a rotary evaporator and the residue was washed with water and extracted with chloroform. The organic extract was dried over magnesium sulfate, filtered, and topped on a rotary evaporator to give 0.9 gram of viscous residue. Chromatography on alumina with ethylacetate/ethanol gave fractions containing a single component (as monitored by thin layer chromatography). These fractions were combined and concentrated on a rotary evaporator to give 0.16 gram of oily residue which partially crystallized on cooling. Recrystallization from ether gave 0.08 gram of white crystals of 3-[3-(1,1-dimethylethyl)-5-isoxazolyl]-4,5-dihydroxy-1-methyl-2-imidazolidinone, M.P. 153°–156° C., which had mass, infrared and NMR spectra consistent with the desired product.

EXAMPLE III

Synthesis of 3-[5-(1,1-dimethylethyl)-3-isoxazolyl]-4,5-dihydroxy-1-methyl-2-imidazolidinone a. Formation of 1-[5-(1,1-dimethylethyl)-3-isoxazolyl]-3-methylurea

A 50 milliliter flask with a magnetic stirring bar, addition funnel, thermometer and condenser/drying tube was charged with 3.0 grams (0.021 mole) of 5-(1,1-dimethylethyl)-3-isoxazolamine, a few crystals of 4-dimethylaminopyridine and 20 milliliters of benzene. The funnel was charged with 2.3 grams (0.040 mole) of methyl isocyanate in 5 milliliters of benzene, which was added dropwise over five (5) minutes. After standing overnight, the mass of crystals which formed was isolated by filtration, washed with hexane, and air dried to give 3.0 grams of white powder of 1-[5-(1,1-dimethylethyl)-3-isoxazolyl]-3-methylurea, M.P. 188°–189° C.

b. Formation of 3-[5-(1,1-dimethylethyl)-3-isoxazolyl]-4,5-dihydroxy-1-methyl-2-imidazolidinone To a solution of 2.0 grams (0.010 mole) of 1-[5-(1,1-dimethylethyl)-3-isoxazolyl]-3-methylurea in 50 milliliters of 95 percent ethanol was added 7.3 grams of a 40 percent aqueous glyoxal solution which had been previously adjusted to pH 7 with dilute sodium hydroxide solution. After standing at room temperature overnight, the solution was topped on a rotary evaporator to give an oily residue which was extracted with two 20 milliliter portions of chloroform. The extract was washed with saturated sodium chloride solution, filtered through silicone-treated paper, and concentrated on a rotary evaporator to give 2.0 grams of oily residue. Crystallization from ether gave 0.4 grams of white crystals of 3-[5-(1,1-dimethylethyl)-3-isoxazolyl]-4,5-dihydroxy-1-methyl-2-imidazolidinone, M.P. 153°–157° C., which had consistent mass, infrared and NMR spectra.

INTERMEDIATE COMPOUNDS

The compounds represented by Formula V possess some herbicidal properties, but in addition, are very useful because they are the intermediates for the synthesis of the novel compounds represented by Formula I.

APPLICATIONS OF THE COMPOSITIONS AGAINST WEEDS

The novel compounds of Formula I are particularly valuable for weed control because they are toxic to many species and groups of weeds and are relatively nontoxic to many beneficial plants. The exact amount of one or more of the compounds required depends upon a variety of factors, including the hardiness of the particular weed species, the weather, the type of soil, the method of application, the kind of beneficial plants in the same area, and the like. Thus, while the application of up to only about one or two ounces of active compound per acre may be sufficient for good control of a light infestation of weeds growing under adverse conditions, the application of 0.2 pounds to 10 pounds or more of an active compound of Formula I per acre may be required for good control of a dense infestation of hardy perennial weeds growing under favorable conditions.

a. Examples of Weeds Which May Be Controlled by the Compounds Described Herein Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds. It is believed that the compositions set forth herein, when applied in a herbicidally effective amount may control field pennycress, ryegrass, goosegrass, chickweed, purslane, smartweed, knotweed, wild buckwheat, kochia, medic, corn cockle, ragweed, sowthistle, croton, cuphia, dodder, fumitory, groundsel, hempnettle, knawel, spurge, spurry emex, jungle rice, pondweed, dogfennel, carpetweed, bedstraw, ducksalad, naiad, chestgrass, fall panicum, witchgrass, switchgrass, watergrass, teaweed, wild turnip and sprangletop; biennials such as wild carrot, matricaria, wild barley, campion, chamomile, burdock, mullein, roundleaved mallow, bull thistle, houndstongue, moth mullein, and purple start thistle; or perennials such as white cockle, perennial ryegrass, quackgrass, Canada thistle, bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania bulrush, cat-tail, winter-cress, horsenettle, nutsedge, milkweed and sicklepod.

However, the important weeds of the genera against which most of the compounds of the invention, particularly the preferred compounds described herein, and particularly the most preferred compound, are most effective preemergence and/or postemergence at 2 pounds per acre are: Sida, Datura, Brassica, Sorghum, Sesbania, Ipomoea, Avena, Abutilon, Setaria, Echinochloa and Digitaria weed species against which the compounds of the invention, particularly the most preferred compound, are most effective are: *Sida spinosa* (L) (teaweed), *Datura stramonium* (jimsonweed), *Brassica kaber* (wild mustard), *Setaria glauca* (L) (yellow foxtail), *Gossypium hirsutum* (L) (cotton as a weed), *Sorghum halepense* (johnsongrass), *Sesbania* spp. (coffeeweed), *Ipomoea purpurea* (L) Roth (tall morningglory), *Avena fatua* (wild oats), *Abutilon theophrasti* (L) (velvetleaf), *Echinochloa crusgalli* (L), (barnyardgrass), and [*Digitaria sanguinalis* (L) (crabgrass, large), preemergence].

The most preferred compound, 3-[5-(1,1-dimethylethyl)-3-isoxazolyl]-1-methyl-4-hydroxy-2-imidazolidinone, is very effective against the above-mentioned genera and species of weeds, as well as being safe to use on rice, when applied preemergence at rates of up to 0.5 pound per acre. At preemergence rates as low as 0.5 pound per acre, the compound 3-[5-(1,1-dimethylethyl)-3-isoxazolyl]-1-methyl-4-hydroxy-2-imidazolidinone stunts and slows the growth of *Cyperus esculentus* (L) (yellow nutsedge).

b. Description of the Method of Controlling Weeds

As used herein and in the Claims, the method of controlling the weeds comprises contacting the weeds with a herbicidally effective amount of a compound represented by the graphic formula described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge or after they emerge, or both before and after they emerge, with one or more of the compounds represented by the general Formula I described herein. The phrase "herbicidally effective amount" refers to that amount required under the environmental conditions in order to effectively control, that is, by which the weeds are injured so as not to be able to recover from the application of the compound, or to be killed by the compound.

c. General Application of the Compounds

For practical use as herbicides, the compounds of this invention are generally incorporated into herbicidal formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules or wettable powders or they can be liquids such as solutions, aerosols or emulsifiable concentrates.

For example, dusts can be prepared by grinding and blending the active compound with a solid inert carrier such as the talcs, clays, silicas, prophyllite, and the like.

Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust composition.

In some cases, the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprises an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifiers systems, an inverted emulsion (water in oil) can be prepared for direct application to weed infestations.

A typical herbicidal formulation according to this invention is illustrated by the following example, in which the quantities are in parts by weight.

EXAMPLE IV

PREPARATION OF A DUST

| Product of Example I | 10 |
|---|---|
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

d. Mixtures of Compounds Alone or in Mixtures

Although all of the compounds described herein and represented by the general formula described herein are useful as herbicides, some of these are preferred and are better for applications against weeds. In general, all of the compounds described herein may be used either alone or together in mixtures. When used in mixtures, the amount of ratio of one compound to another may vary from 0.01 to 100.

e. Manner of Application of the Compounds of This Invention

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulations will comprise from about 0.05 to about 95 percent by weight of the active compounds of this invention. In a preferred embodiment of this invention, the herbicidal formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples of Other Pesticides and Herbicides for Combinations

The other herbicides, defoliants, desiccants and plant growth inhibitors, with which the compounds of this invention can be used in the herbicidal formulations to control weeds, can include: chlorophenoxy herbicides such as 2,4-D, 2,4,5-T, MCPA, MCPB, 4-(2,4-DB), 2,4-DEB, 4-CPB, 4-CPA, 5-CPP, 2,4,6-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEBC, pebulate, vernolate and the like; substituted urea herbicides such as norea, siduron, dichloroal urea, chloroxuron, cycluron, fenuron, monuron, monuron TCA, diuron, linuron, monolinuron, neburon, buturon, trimeturon, and the like; symmetrical triazine herbicides such as simazine, chlorazine, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as TCA, dalapon, 2,3-dichloropropionic acid, 2,2-TPA, and the like; chlorinated benozic acid and phenylacetic acid herbicides such as 2,3,6-TBA, 2,3,5,6-TBA, dicamba, tricamba, ambien, fenac, PBA, 2-methoxy-3,6-dichlorophenylacetic acid, 3-methoxy-2,6-dichlorophenylacetic acid, 2-methoxy-3,5,6-trichlorophenylacetic acid, 2,5-dichloro-3-nitrobenzoic acid, dual, metribuzin and the like; and such compounds as aminotriazole, maleic hydrazide, phenyl mercuric acetate, endothall, biuret, technical chlordane, dimethyl 2,3,5,6-tetrachlorotetraphthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EXD, ioxynil, isocil, potassium cyanate, MAA, MAMA, MCPES, MCPP, MH, molinate, NPA, paraquat, PCP, picloram, DPA, PCA, phrichlor sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides and other derivatives whenever applicable to the particular parent compounds.

g. Examples of Herbicidal Control

The following examples illustrate the utility of the compositions described herein for the control of weeds.

These tests described herein were conducted in a laboratory under laboratory conditions, using standard laboratory procedures.

EXAMPLE V

When the compound of 3-[5-(1,1-dimethylethyl)-3-isoxazlyl]-1-methyl-4-hydroxy-2-imidazolidinone (Example I) was applied postemergence at two (2) pounds per acre to the weed species: *Sida spinosa* (teaweed), *Sesbania spp.* (coffeeweed), *Gossypium hirsutum* (L) (cotton as a weed), *Setaria glauca* (L) (yellow foxtail), *Abutilon theophrasti* (L) (velvetleaf), *Echinochloa crusgalli* (L) (barnyardgrass), *Avena fatua* (L) (wild oats), *Datura stramonium* (L) (jimsonweed), *Sorghum halepense* (L) (johnsongrass), *Ipomoea purpurea* (L) Roth (morningglory, tall), and *Brassica kaber* (L) (wild mustard), at the end of twenty-one (21) days, many of the weeds were so severely injured that they could not recover, and others were killed.

EXAMPLE VI

When the compound 3-[5-(1,1-dimethylethyl)-3-isoxazolyl]-1-methyl-4-hydroxy-2-imidazolidinone (Example I) was applied preemergence at two (2) pounds per acre to the weed species: *Sida spinosa* (teaweed), *Sesbania spp.* (coffeeweed), *Digitaria sanguinalis* (L) (crabgrass, large), *Setaria glauca* (L) (yellow foxtail), *Abutilon theophrasti* (L) (velvetleaf), *Echinochloa crusgalli* (L) (barnyardgrass), *Avena fatua* (L) (wild oats), *Datura stramonium* (L) (jimsnweed), *Sorghum halepense* (L) (johnsngrass), *Ipomoea purpurea* (L) Roth (morningglory, tall), and *Brassica kaber* (L) (wild mustard), all of the weeds were so severely injured that they could not recover, and others were killed, at the end of twenty (20) days.

EXAMPLE VII

When the compound 3-[3-(1,1-dimethylethyl)-5-isoxazolyl]-4,5-dihydroxy-1-methyl-2-imidazolidinone of Example II was applied postemergence at one (1) pound per acre against the weed species: *Sida spinosa* (teaweed), *Datura stramonium* (L) (jimsonweed), *Brassica kaber* (L) (wild mustard), *Setaria glauca* (L) (yellow foxtail), *Gossypium hirsutum* (L) (cotton, as a weed), *Sesbania spp.* (coffeeweed), *Abutilon theophrasti* (L) (velvetleaf), *Ipomoea purpurea* (L) Roth (moringglory, tall), and *Avena fatua* (L) (wild oats), at the end of twenty (20) days, most of the weeds were killed while others were so severely injured that they could not recover.

EXAMPLE VIII

When the compound 3-[3-(1,1-dimethylethyl)-5-isoxazolyl]-4,5-dihydroxy-1-methyl-2-imidazolidinone (Example II) was applied preemergence at one (1) pound per acre against the weed specia: *Datura stramonium* (L) (jimsonweed), *Brassica kaber* (L) (wild mustard), *Setaria glauca* (L) (yellow foxtail), *Digitaria sanguinalis* (L) (crabgrass, large), *Avena fatua* (L) (wild oats), and *Echinochloa crusgalli* (L) (barnyardgrass), at the end of twenty (20) days, most of the weeds were killed, while others were so severely injured that they could not recover.

EXAMPLE IX

When the compound 3-[5-(1,1-dimethylethyl)-3-isoxazolyl]-4,5-dihydroxy-1-methyl-2-imidazolidinone of Example III was applied preemergence at one (1) pound per acre against the weed species: *Sida spinosa* (teaweed), *Datura stramonium* (L) (jimsonweed), *Sesbania spp.* (coffeeweed), *Abutilon theophrast* (L) (velvetleaf), *Ipomoea purpurea* (L) Roth (morningglory, tall), and *Avena fatua* (L) (wild oats), at the end of twenty (20) days, most of the weeds were so severely injured that they could not recover and some were killed.

While the invention has been described with reference to the specific details of certain illustrative embodiments, it is not intended that it shall be limited thereby except insofar as such details appear in the accompanying claims.

I claim:

1. A method of controlling weeds which comprises contacting the weeds with a herbicidally effective amount of a compound of Formula I:

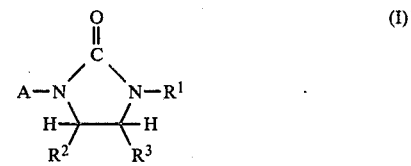

wherein:
A is

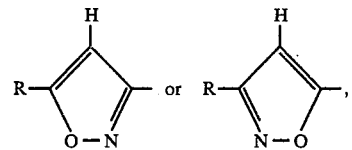

where
R is an alkyl of up to six carbon atoms,
  an alkenyl of up to five carbon atoms,
  an alkynyl of of up to five carbon atoms,
  a cycloalkyl selected from the group consisting of cyclopropyl, cyclobutyl, cyclopentyl, and cyclohexyl,
  a haloalkyl of up to six carbon atoms,
  $-R^4-O-R^5$ or $-R^4-S-R^5$, where $R^4$ is an alkylene of up to six carbon atoms and $R^5$ is an alkyl of up to six carbon atoms, or

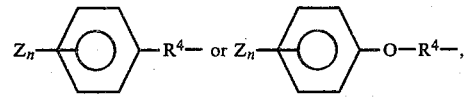

where Z is nitro ($NO_2$), chloro (Cl), bromo (Br), fluoro (F), or $R^5$, and n is 0, 1, 2, or 3;
$R^1$ is an alkyl of up to three carbon atoms or allyl;
$R^2$ is hydroxy (OH), chloro (Cl), or bromo (Br); and
$R^3$ is hydrogen (H), an alkyl of up to four carbon atoms, allyl, or hydroxy (OH).

2. The method as recited in claim 1, which is 3-[3-(1,1-dimethylethyl)-5-isoxazolyl]-4,5-dihydroxy-1-methyl-2-imidazolidinone.

3. The method as recited in claim 1, which is 3-[5-(1,1-dimethylethyl)-3-isoxazolyl]-4,5-dihydroxy-1-methyl-2-imidazolidinone.

4. The method as recited in claim 1, which is 3-[5-(1,1-dimethylethyl)-3-isoxazolyl]-4-hydroxy-1-methyl-2-imidazolidinone.

* * * * *